(12) United States Patent
Meitner

(10) Patent No.: US 8,434,337 B2
(45) Date of Patent: May 7, 2013

(54) METHOD AND APPARATUS FOR BENDING A GUIDE POST USED IN FORMING A TEMPLATE FOR LOCATING A DENTAL IMPLANT HOLE

(76) Inventor: Sean W. Meitner, Middlesex, NY (US)

( * ) Notice: Subject to any disclaimer, the term of this patent is extended or adjusted under 35 U.S.C. 154(b) by 246 days.

(21) Appl. No.: 12/848,712

(22) Filed: Aug. 2, 2010

(65) Prior Publication Data
US 2012/0028213 A1 Feb. 2, 2012

(51) Int. Cl.
*B21C 51/00* (2006.01)
*G01B 5/24* (2006.01)
*G01B 3/56* (2006.01)

(52) U.S. Cl.
USPC .................. 72/31.1; 33/412; 33/534

(58) Field of Classification Search .................. 72/31.04, 72/31.05, 31.1, 459; 33/1 N, 412, 534, 538
See application file for complete search history.

(56) References Cited

U.S. PATENT DOCUMENTS

| | | | |
|---|---|---|---|
| 2,361,565 A * | 10/1944 | Reed | 33/1 N |
| 2,434,320 A | 1/1948 | Karlstrom | |
| 2,737,835 A * | 3/1956 | Herz | 72/31.1 |
| 3,011,259 A | 12/1961 | Baum | |
| 3,407,503 A | 10/1968 | Nealon | |
| 3,413,724 A | 12/1968 | Segal | |
| 3,600,810 A | 8/1971 | Marshall et al. | |
| 4,060,899 A | 12/1977 | Sauter | |
| 4,109,383 A | 8/1978 | Reed et al. | |
| 4,277,237 A | 7/1981 | Dermer | |
| 5,007,836 A | 4/1991 | Gayso | |
| 5,015,183 A | 5/1991 | Fenick | |
| 5,133,660 A | 7/1992 | Fenick | |
| 5,320,529 A | 6/1994 | Pompa | |
| 5,337,489 A * | 8/1994 | Mustafa | 33/534 |
| 5,556,278 A | 9/1996 | Meitner | |
| 5,800,168 A | 9/1998 | Cascione et al. | |
| 5,833,693 A | 11/1998 | Abrahami | |
| 5,842,859 A | 12/1998 | Palacci | |
| 5,967,777 A | 10/1999 | Klein et al. | |
| 6,634,883 B2 | 10/2003 | Ranalli | |
| 6,672,869 B2 | 1/2004 | Rabenstein et al. | |

(Continued)

FOREIGN PATENT DOCUMENTS

DE 4111278 A1 * 10/1992
WO 9426200 A1 11/1994

OTHER PUBLICATIONS

Patent Cooperation Treaty, International Search Report, 201-03-19, PCT/US2011/046104, 10 pages.
U.S. Appl. No. 12/945,442, Meitner, filed Nov. 12, 2010.

*Primary Examiner* — Teresa M Ekiert
(74) *Attorney, Agent, or Firm* — Stephen B. Salai, Esq.; Jodi A. Reynolds, Esq.; Harter Secrest & Emery LLP

(57) ABSTRACT

An apparatus and method for bending a guide post used in forming a template for locating dental implant hole. The guide post includes at least one face on a distal end for registering the orientation of the guide post. The apparatus includes a base plate having protractor-like indicia, a supporting block attached to the base plate, the supporting block having an aperture for receiving a distal end of the guide post, and a stylus received by a proximal end of the guide post, the stylus extending towards the protractor-like indicia.

10 Claims, 6 Drawing Sheets

U.S. PATENT DOCUMENTS

| | | |
|---|---|---|
| 7,097,451 B2 | 8/2006 | Tang |
| 7,121,827 B2 | 10/2006 | Lampert |
| 7,322,821 B1 | 1/2008 | Lin |
| 7,845,943 B2 | 12/2010 | Meitner |

* cited by examiner

METHOD AND APPARATUS FOR BENDING A GUIDE POST USED IN FORMING A TEMPLATE FOR LOCATING A DENTAL IMPLANT HOLE

CROSS-REFERENCE TO RELATED APPLICATIONS

None.

STATEMENT REGARDING FEDERALLY SPONSORED RESEARCH OR DEVELOPMENT

None.

REFERENCE TO A "SEQUENCE LISTING"

Not applicable.

BACKGROUND OF THE INVENTION

1. Field of the Invention

The present invention relates to a bending tool for a guide post used to form a template for locating a dental implant hole (osteotomy) in a patient's jawbone and methods related thereto.

2. Description of Related Art

To determine the appropriate location for drilling a hole in a patient's jawbone to insert an endosteal root form implant in a patient's mandible or maxilla, a dentist or oral surgeon typically creates a dental cast of the patient's jaw and creates a template from the cast to guide the drill when performing an osteotomy.

More specifically, a dental cast impression of a patient's mandible and/or maxilla, including the edentulous space is created. A hole is drilled into the dental cast approximately in the location and orientation of the hole corresponding to a desired location of the dental implant osteotomy is estimated. Then a guide post is inserted into the hole and a sleeve is attached to the guide post. A template-forming molding material is applied to a portion of the dental cast and to a portion of an outer surface of the sleeve and allowed to cure. Once cured, the template is removed from the dental cast and placed in the patient's jaw in order to guide a drill for planning the endosteal root form implant.

A problem, however, is that the location and orientation of the osteotomy may need to be adjusted to correctly align the osteotomy with the alveolar bone and other anatomic structures, such as the roots of the adjacent teeth nerves, and sinuses. It is important to accurately locate the osteotomy in the jawbone so that the implant is sufficiently anchored in the bone structure.

It is known in dental surgery to make a dental cast impression of the patient's mandible and/or maxilla in order to design or select the appropriate prosthetic device. Moreover, it is known to use the diagnostic tooth set-up or wax-up on a cast to determine a desirable tooth position in the final restoration. In locating and creating the hole for a dental implant, however, the most commonly used methods involve estimating the appropriate position of the implant, drilling a hole in a dental cast at an estimated location and orientation to form a template and drilling an osteotomy in a patient's jaw at the same location and orientation.

What is needed then is a method and apparatus for accurately, inexpensively, and conveniently locating an osteotomy for an endosteal root form implant in the mandible and/or maxilla of a patient using a template having an accurately aligned sleeve.

BRIEF SUMMARY OF THE INVENTION

It is therefore an object of the invention to provide a method for orienting an implant osteotomy in the mandible and/or maxilla of a patient.

It is another object of the invention to provide an apparatus for accurately bending a guide post to create a template for locating one or more dental implant osteotomies in a patient's mandible and/or maxilla.

It is a further object of the invention to provide a template for accurately locating a dental implant osteotomy in a patient's mandible and/or maxilla.

In accordance with the foregoing, an embodiment of the present invention includes an apparatus for bending a guide post used in forming a template for locating dental implant hole, the guide post having at least one face on a distal end for registering the orientation of the guide post, comprising a base plate having protractor-like indicia, a supporting block attached to the base plate, the supporting block having an aperture for receiving a distal end of the guide post, and a stylus received by a proximal end of the guide post, the stylus extending towards the protractor-like indicia.

Another embodiment of the invention includes a method for making a template for locating a dental implant osteotomy in a patient's mandible or maxilla. The method comprises forming a dental cast of the patient's mandible or maxilla including the edentulous space and drilling a hole into the dental cast for receiving a guide post wherein the location of the hole corresponds to an approximate location of the dental implant osteotomy. A first template is formed, including a sleeve attached to molding material. A first and second x-ray image of the patient's mouth with the first template is taken wherein a virtual implant is moved to overlay the sleeve in the first and second x-ray images. The virtual implant is positioned in the desired location of the prosthetic tooth on the first and second images, taking into consideration the bone structure and other anatomic structures, such as the roots of the adjacent teeth, nerves and sinuses, which must be avoided. A longitudinal axis of the virtual implant and a longitudinal axis of the sleeve are determined. Then, an angle between the longitudinal axis of the virtual implant and the longitudinal axis of the sleeve is measured. The guide post is then bent at the measured off-axis angle and the bent guide post is then inserted into the hole in the dental cast. The sleeve is attached to the guide post and a template-forming, molding material is applied to a portion of the dental cast and to a portion of an outer surface of the sleeve to form a second template that is used in the patient's mouth to perform the actual osteotomy at the new desired position.

The method thus described is not limited to the location of a single implant osteotomy, but the technique applies equally to locating more than one implant osteotomy in one or more edentulous spaces in a patient's mouth.

The invention will now be described in detail in terms of the drawings and the description which follow.

BRIEF DESCRIPTION OF THE SEVERAL VIEWS OF THE DRAWING(S)

DETAILED DESCRIPTION OF THE INVENTION

At the outset, it should be appreciated that the use of the same reference number throughout the several figures designates a like or similar element.

Figure 1:
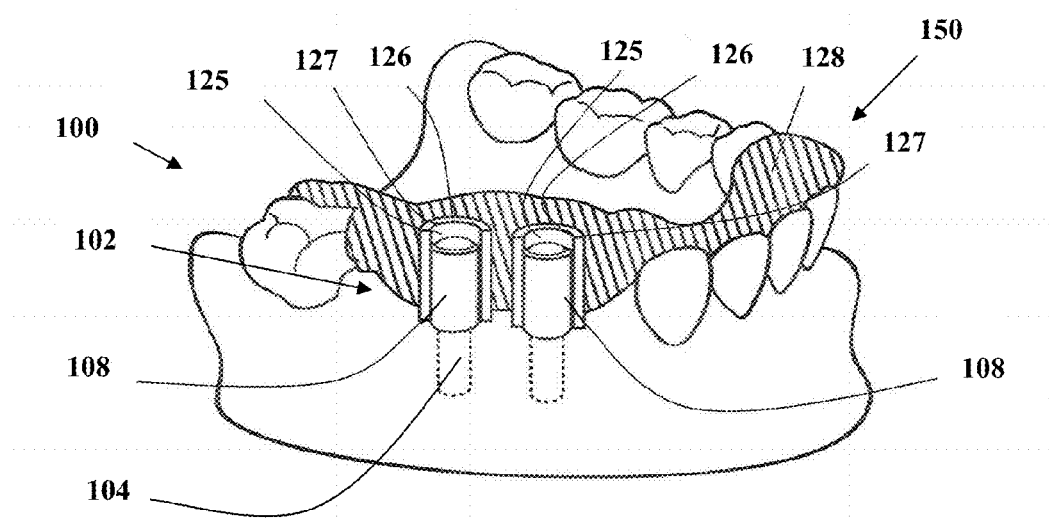
FIG. 1 is a perspective view of a dental cast showing a guide post and a first template formed by a sleeve and a molding material cured thereto.
Figure 2:
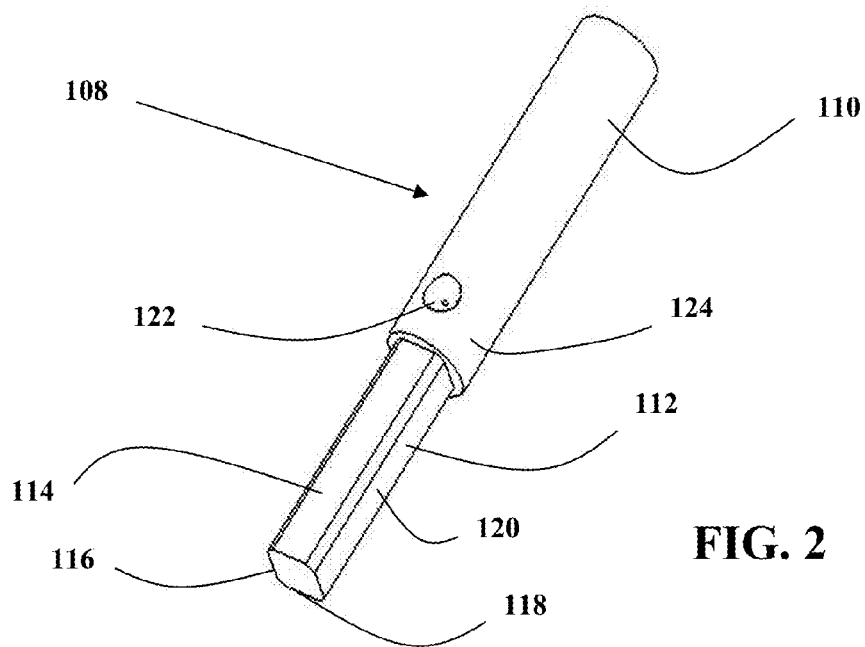
FIG. 2 is perspective view of a guide post having a proximal and distal end and an indicator for registering the orientation of the guide post.

Referring now to the figures, FIG. 1 is a perspective view of a dental cast impression 100 of a patient's mandible or maxilla jawbone having an edentulous space 102 where at least one tooth has been lost and is to be replaced by an endosteal root form implant. In addition to the edentulous space 102, the dental cast impression 100 includes the adjacent regions including the lingual surface of a tooth adjacent one side of the edentulous space wherein the implant will be located and/or an occlusal surface of a tooth adjacent one side of the edentulous space where the implant will be located, and is typically made in alginate and poured up, preferably, in cast stone or plaster. Cast stone is preferred over die stone because the relatively softer cast stone permits the drill bit for making the implant guide hole in the dental cast 100, as will be more fully described below.

An appropriate position of the dental implant is estimated and a hole 104 is drilled into the cast 100 with a drill bit. To estimate the appropriate position of the dental implant, the optimum location of the prosthetic implant is evaluated, in part, on the height and orientation of the adjacent and opposing teeth, the spacing between the edentulous space 102, and the height and width of the patient's bone. Preferably, the hole 104 is made with a standard, inexpensive, 3/32" diameter drill bit which conveniently fits in a dental laboratory handpiece. The depth of the hole 104 is preferably at least 10 mm deep. The drill bit is removed, leaving the hole 104 in the cast that captures the proposed longitudinal axis of the proposed osteotomy. A cylindrical, straight guide post 108 is inserted into the hole 104 in the cast. The guide post 108 includes an upper shaft at the proximal end 110 and a lower shaft at the distal end 112. The distal end 112 may include one or more, preferably four flat surfaces 114, 116, 118, and 120, at 90 degree angles, that is, 90, 180, 270 and 360 degrees, representing the mesial, distal, buccal and lingual/palatal surfaces, respectively, of the proposed tooth implant. One of the four flat face surfaces 114, 116, 118, or 120 of the distal end 112 of the guide post 108 includes an indicator 122 for registering the orientation of the guide post 108. For example, in FIG. 1, the medial portion 124 of the guide post 108 includes a depression aligned in the center of one of the four flat surfaces of the guide post, for instance the buccal surface 118. Although a depression is shown, it should be appreciated by those having ordinary skill in the art, that other types of indicators can be used, including but not limited to, engraved markings, paint markings, and ink markings.

Figure 3:
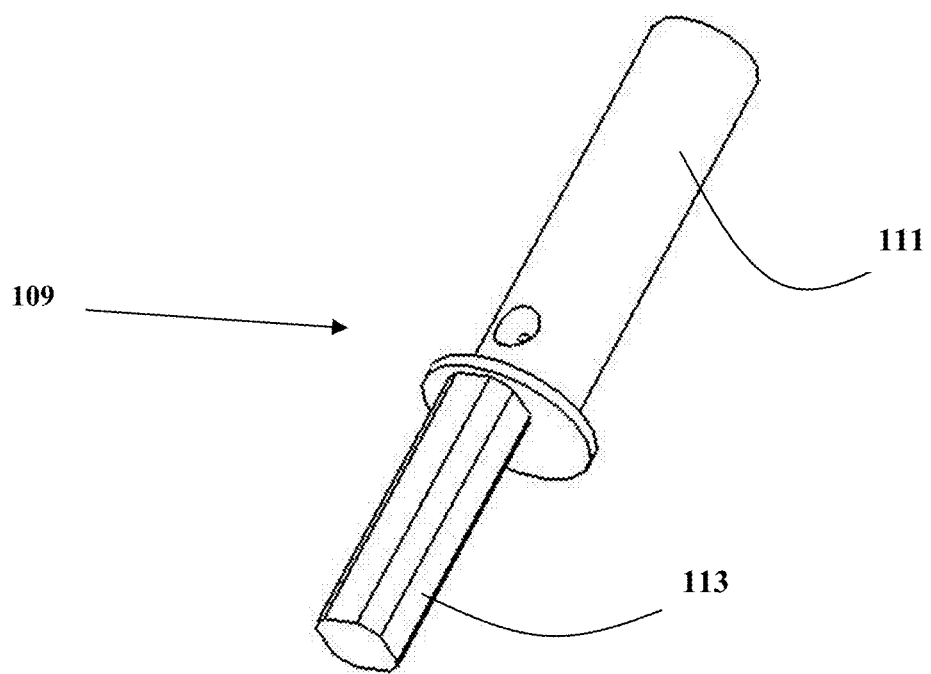
FIG. 3 is a perspective view of a guide post having a proximal and distal end, wherein the distal end is offset from the proximal end.
Figure 4A:
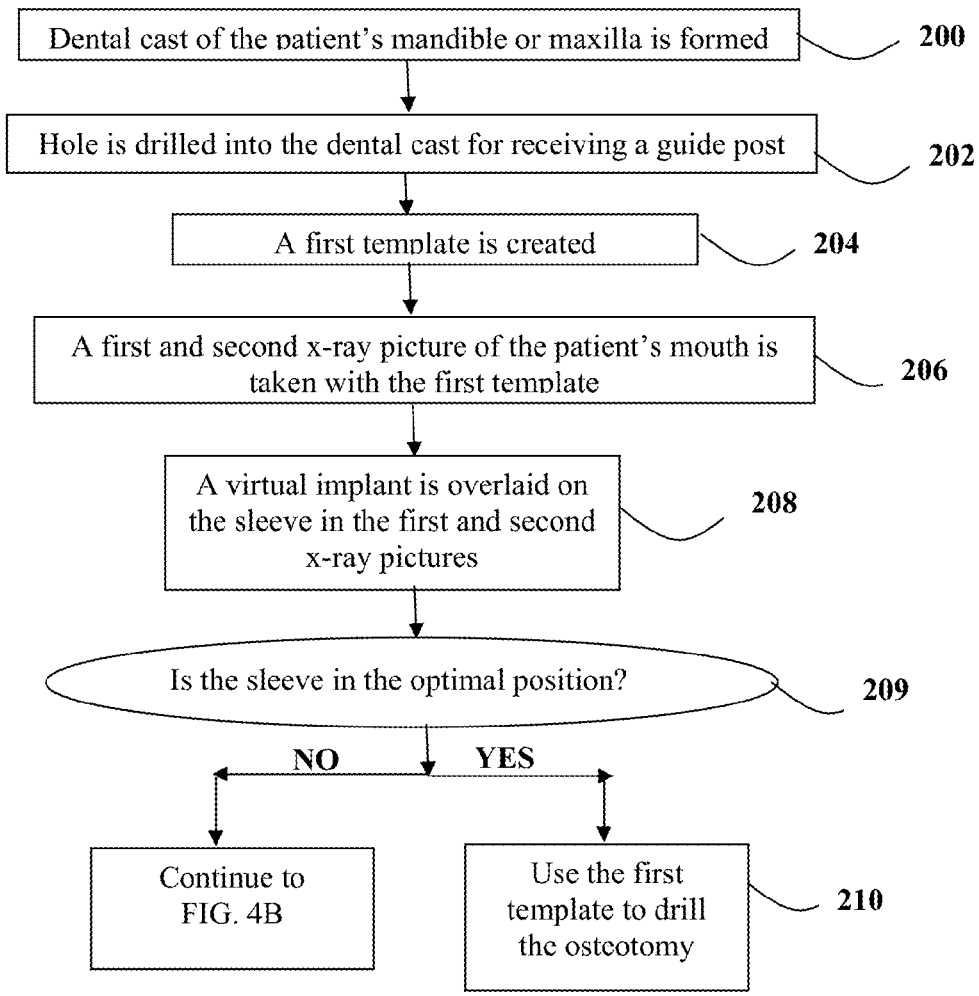
FIGS. 4A and 4B illustrate one embodiment of the method of the invention.
Figure 4B:
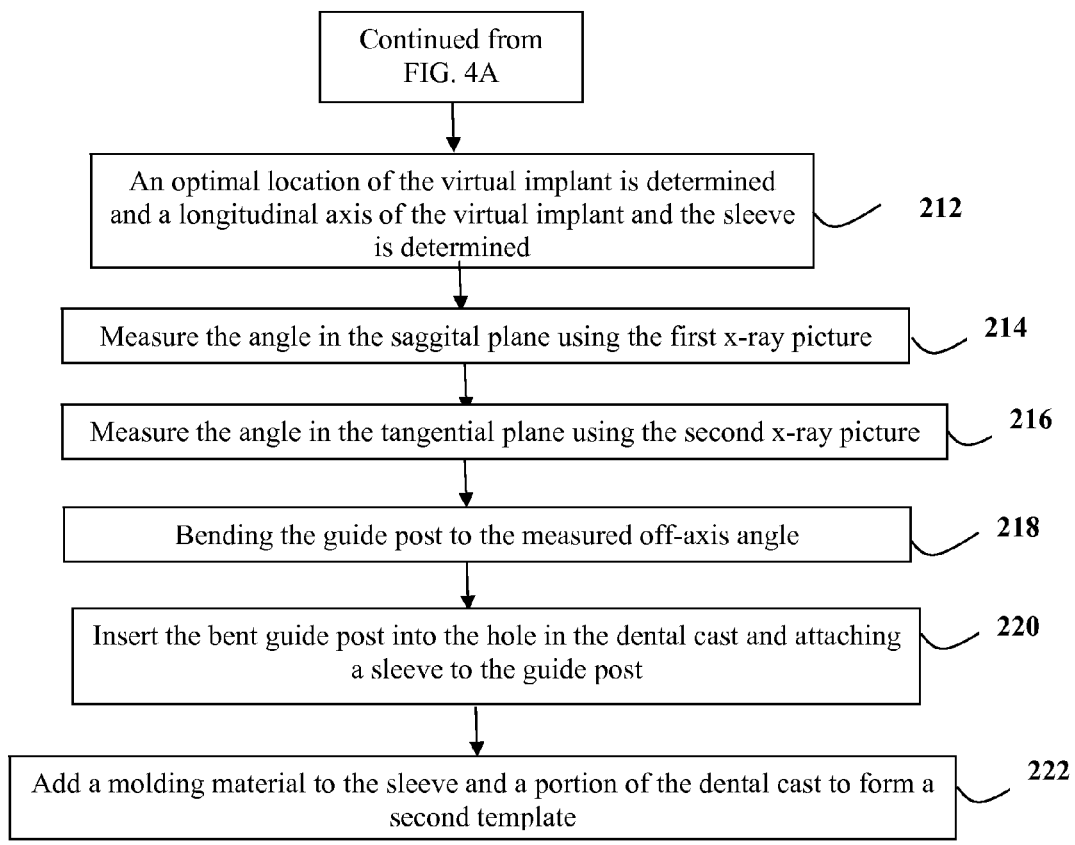

As shown in FIG. 3, an offset guide post 109 may be used, which includes a distal end 113 offset from the proximal end 111 of the guide post 109.

A guide sleeve 126 is placed over the guide post 108 or 109 to serve as a diagnostic guide for the drill and eventual creation of the hole that will be prepared in the patient's mandible or maxilla to place the implant. The guide sleeve 126 can be an open guide sleeve 127 that has a longitudinal gap 125 or it can be a closed guide sleeve, without a longitudinal gap (not shown), depending on whether there is enough space in a patient's mouth to insert a drill through the top of the guide sleeve 126. The evaluation of the position of the guide sleeve 126 in the template in relation to the underlying bone can be determined with a 3D X-Ray device, for example, a Galileos manufactured by Sirona. The correction of the longitudinal axis of the guide sleeve 126 often requires altering the angle of the surgical guide sleeve 126 in one or two planes or maintaining the same angles and bodily moving the position of the guide sleeve 126 a distance in any two planes or four directions, that is, mesial (forward), distal (back), buccal (side) or lingual/palatal (side).

More specifically, as shown in FIG. 3, a dental cast of the patient's mandible or maxilla including the edentulous space is formed according to step 200. Then a hole is drilled into the dental cast for receiving a guide post wherein the location of the hole corresponds to a desired location of the dental implant osteotomy as set forth in step 202. According to step 204, a first template 150 having a sleeve attached to cured molding material is formed. Then, as indicated in step 206, a first and second x-ray image of the patient's jaw is taken with the first template. That is, a CAT scan (computer axial tomography) image or cone beam x-ray image is taken and the images from the x-rays are used to calculate any changes that need to be made in the position or angle of the guide sleeve.

More specifically, according to step 208, a virtual implant is overlaid on the sleeve in the first and second x-ray images and it is determined whether the sleeve is in the optimal position 209 such that the virtual implant will be in the desired location if the first template is used. If the sleeve aligns with the desired location of the virtual implant, the first template can be used according to step 210. If the virtual implant is not in the desired location when aligned with the sleeve, the virtual implant is positioned in the optimal location. The optimal location and alignment of the guide sleeve is determined based on the space of the alveolar bone and other anatomic structures such as the roofs of the adjacent teeth, nerves and sinuses. According to step 212, a longitudinal axis of the virtual implant and of the sleeve is determined using Galaxis, Sirona software. The position and alignment of the guide sleeve are viewed in two dimensions, bucco-lingually, in a tangential slice and mesio-distally in a saggittal slice. If the longitudinal axis of the virtual implant does not correspond with the optimal position of the implant, the longitudinal axis of the virtual implant is changed so that the virtual implant is in the optimal position. Using the software, two lines are established: the first line indicates the central longitudinal axis of the virtual implant and the second line indicates the central longitudinal axis of the sleeve. The intersection of these two lines form an angle that can be measured in the first x-ray image taken in the saggital plane using the angle tool of the Galaxis software according to step 214. The angle is also measured in the second x-ray image taken in the tangential plane as set forth in step 216. This angle indicates the change needed to be made to the position of the guide sleeve to correctly place the dental implant. That is, the angle indicates the amount the guide post needs to be bent off-axis to form a template having a sleeve in the correct orientation. Alternatively, two x-ray images, one taken in the saggital plane and the other taken in the tangential plane, can be printed and the angle formed by the first and second line can be measured by superimposing a protractor over the angle. After the guide post is bent according to the measured off-axis angle, as set forth in step 218, the bent guide post is inserted into the hole 104 of the dental cast 100 and a sleeve 126 is attached to the guide post 108 according to steps 220. Then a template-forming molding material 128 is applied to a portion of the dental cast 100 and to a portion of an outer surface of the sleeve and portions of the dental cast to remake template, according to step 222.

Figure 5:
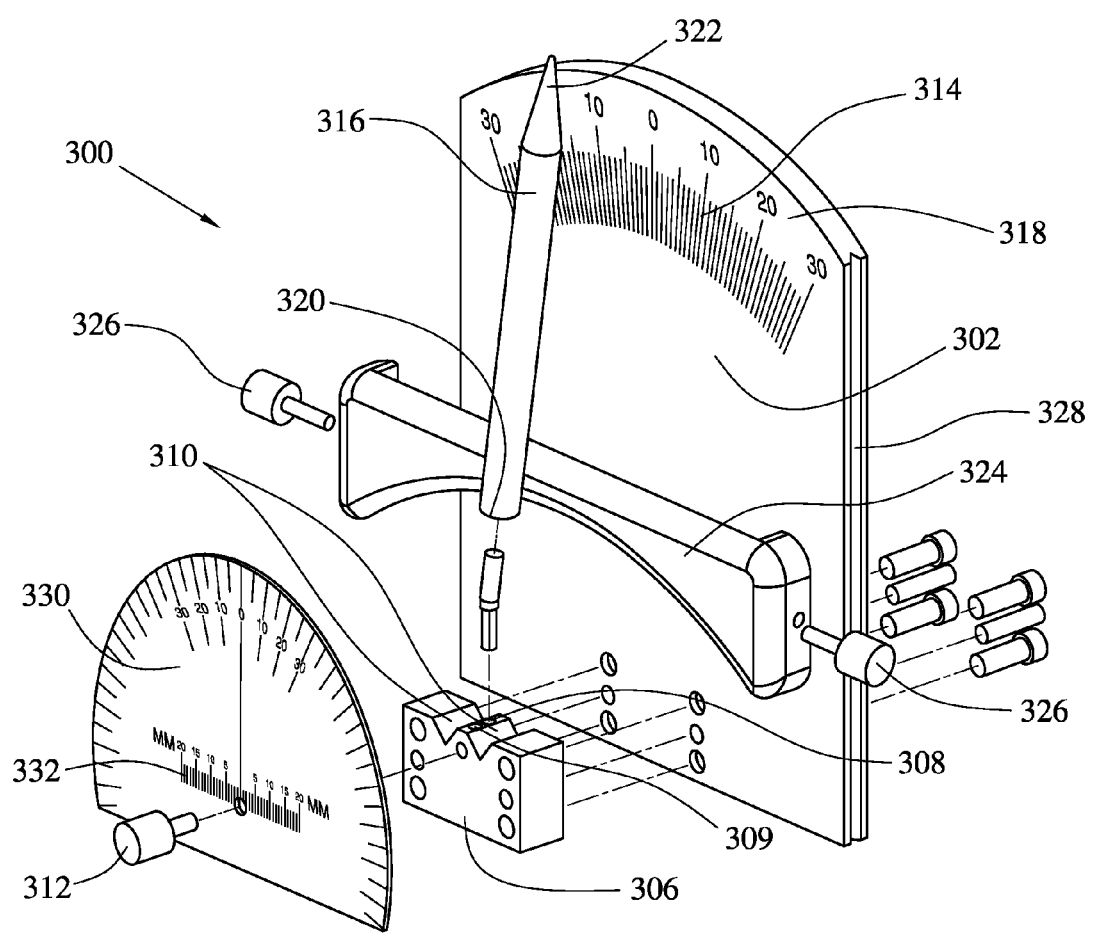
FIG. 5 is an exploded perspective view of the bending apparatus.
Figure 6:
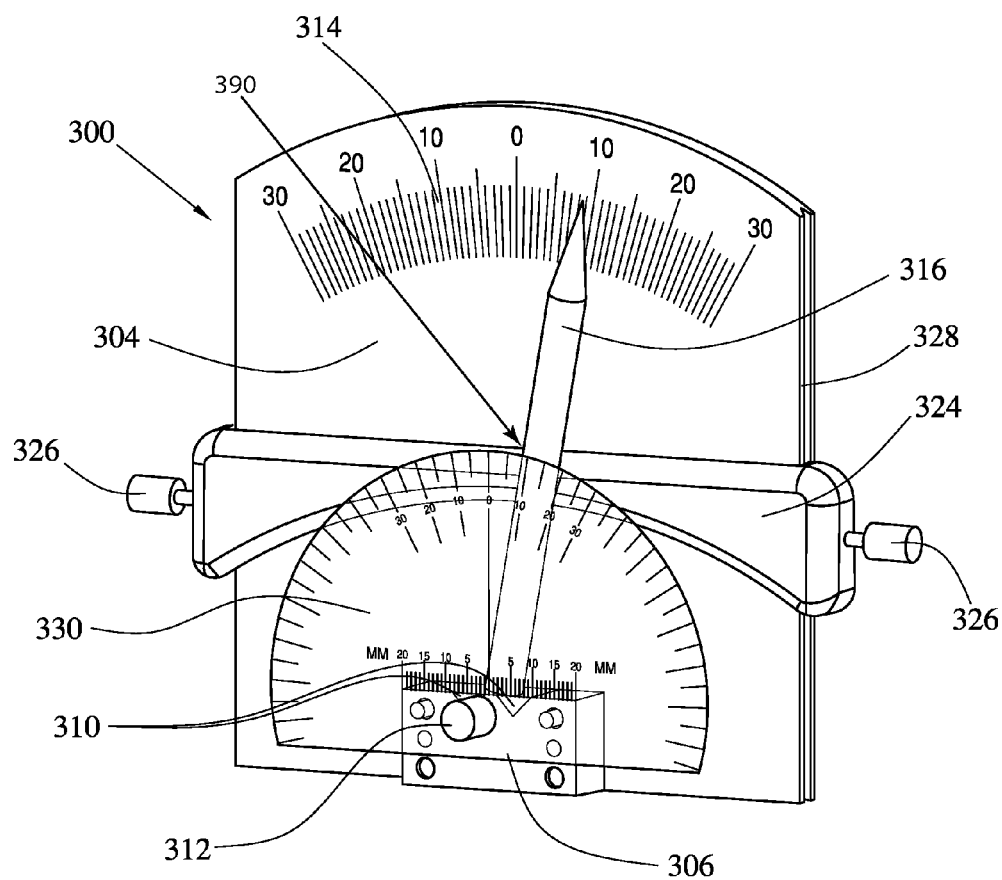
FIG. 6 is perspective view of the bending apparatus being used to perform a second bend.

To bend the guide post, a bending tool apparatus 300 can be used as shown in FIGS. 5 and 6. The bending tool 300 receives the guide post 108 or 109 and allows the guide post 108 or 109 to be bent to a desired angle. More specifically, the bending tool 300 includes a base plate 304 and a supporting block 306 attached to the base plate 304. The supporting block 306 is attached to the base plate 304 via pins or similar attachment means and includes two receiving apertures 308, 309. The supporting block 306 also includes two v-shaped slots 310 to accommodate the edge of the stylus 316 when the stylus 316 is bent to the right or to the left as described in more detail below. The receiving apertures 308, 309 are sized to receive the guide post 108 or 109 and are preferably 3/32" in diameter, although other diameter sizes of guide posts and corresponding receiving apertures are contemplated. The guide post 108 or 109 is inserted into the first receiving aperture 308 most proximate the base plate 304 and is locked into the aperture 308 by a lock 312, such as the central thumb screw as shown in FIGS. 5 and 6. The base plate 304 also includes a first protractor-like indicia 314 positioned near the terminal end 318 of the base plate 304 A stylus 316 includes an at least partially hollow end 320 that is sized to correspond to the diameter of the guide post 108 or 109 and that engages the proximal end 110 of the guide post 108 or 109. The stylus 316 also includes a medial portion 390 and a second end 322 that aligns with the first protractor-like indicia 314 for bending the guide post 108 or 109. The stylus 316 also includes a second end 322 that aligns with the first protractor-like indicia 314 for bending the guide post 108 or 109 through the offaxis angle. Preferably, the second end of the stylus 316 is at least partially pointed to provide a more accurate measurement.

If the x-ray of the first template indicates that the off-axis angle of the guide sleeve 126 must be corrected in two planes, the guide post 108 or 109 must be bent in two planes, for example, bucca-lingually and mesio-distally. Thus, the guide post 108 or 109, having an indicator 122 on the front face surface of the guide post 108 or 109 is placed in the supporting block 306 by inserting it into the aperture 308 and locking into place with lock 312. The first bend is made by placing the stylus 316 over the guide post 108 or 109 and pushing the stylus 316 to the right or to the left. After the first bend is completed, the lock 312 is released and the guide post 108 or 109 is rotated 90 degrees. The guide post is then placed in the aperture 308 and the lock 312 is tightened again. If the guide post is offset, for example, as shown in FIG. 3, the other aperture 309, which is farther away from the surface of the base plate 304, is used. When the guidepost is rotated 90° to made the second bend after the first bend is completed, the position of the stylus 316 moves away from the surface of the base plate 304. To make the second bend at 90° from the first bend, therefore, a support bar 324 is slid down the base plate 304 via lateral set screws 326 that slideably engage grooves 328 along the perimeter edges of the base plate 304. The support bar 324 is slid until it contacts the stylus 316. The lateral set screws 326 are tightened against the grooves 328 in the base plate 304 to lock the support bar 324 into a desired position. In addition, a second protractor device 330 is placed on the base plate 304 and over the supporting block 306 such that the protractor 330 is overlying the surface of the stylus 316. The angle of the second bend is read from this protractor device 330. A second protractor device 330 is needed because the first bend prohibits accurate readings using the first protractor-like indicia 314 since the guide post 108 or 109 will not lay flat against the base plate 304 after the first bend is made. The protractor 330 is temporarily secured in position by pins and/or the lock 312 on the supporting block 306, which pins protrude through two holes in the protractor. However, it should be appreciated by those having ordinary skill in the art that other means can be used to secure the protractor device 330 to the supporting block 306 and these modifications are indented to be included within the spirit and scope of the invention as claimed. The stylus 316 is placed over the guide post 108 or 109 and rotated to the right or left to make the second bend which is in a plane 90° from the first bend. The corrected guide post 108 or 109 is placed back in the dental cast 100 with the indicator 122 position toward the buccal surface. A guide sleeve 126 is now placed over the corrected and accurate guide post 108 or 109 position and a second surgical template is made. The second protractor may include ruler-like indicia 332, for example markings to indicate millimeters, that are used for measuring the offset when an offset guide post 109 as shown in FIG. 3 is required.

There has thus been described an apparatus for bending a guide post used in forming a template for locating a dental implant hole and a method relating thereto. Those skilled in the art will recognize that modifications may be made in the apparatus and method described herein without departing form the true spirit and scope of the invention which accordingly are indented to be limited solely by the appended claims.

The invention claimed is:

1. An apparatus for bending a guide post used in forming a template for locating a dental implant hole, the guide post having at least one face on a distal end for registering the orientation of the guide post, comprising:
    a base plate;
    a supporting block on the base plate, the supporting block having an aperture for receiving a distal end of the guide post;
    a first protractor indicia on the base plate; and
    a stylus having a first end engaging a proximal end of the guide post and a second end aligned with the first protractor indicia for bending the guide post through a first angle as indicated by the first set of protractor indicia.

2. The apparatus of claim 1 further including a stylus support plate slideably engaged on the base plate.

3. The apparatus of claim 1, wherein the stylus includes a medial portion aligned with a second protractor indicia, removably attached to the supporting block, for bending the guide post through a second angle as indicated by the second set of protractor indicia.

4. The apparatus of claim 1, wherein the supporting block includes two v-shaped slots and two apertures for receiving the guide post.

5. The apparatus of claim 4, wherein the supporting block includes a lock for temporarily securing the guide post in one of the apertures.

6. An apparatus for bending a guide post used in forming a template for locating a dental implant hole, the guide post having at least one face on a distal end for registering the orientation of the guide post, comprising:

a base plate;

a supporting block on to the base plate engaging the at least one face of the guide post and capable of holding the guide post in two orientations approximately 90 degrees from one another;

a first protractor indicia on the base plate;

a second protractor indicia on the base plate;

a stylus having a first end engaging a proximal end of the guide post and a second end aligned with the first and second protractor indicia for bending the guide post through a first angle as indicated by the first set of protractor indicia and bending the guide post through a second angle as indicated by the second set of protractor indicia;

a stylus support plate slideably engaged on the base plate; and a lock for temporarily securing the guide post in a desired location.

7. The apparatus of claim 1, wherein the base plate further includes a ruler indicia for measuring an offset of the guide post.

8. The apparatus for bending a guide post of claim 6 wherein the supporting block includes two v-shaped slots and at least two apertures for positioning the guide post in a first or second position.

9. The apparatus for bending a guide post of claim 1 wherein a second protractor indicia is temporarily positioned on the supporting block.

10. An apparatus for bending a guide post used in forming a template for locating dental implant hole, the guide post having at least one face on a distal end for registering the orientation of the guide post, comprising:

a base plate having protractor indicia;

a supporting block attached to the base plate, the supporting block having an aperture for receiving a distal end of the guide post; and a stylus received by a proximal end of the guide post, the stylus extending towards the protractor indicia.

* * * * *